United States Patent
Odedra et al.

(10) Patent No.: US 7,282,119 B2
(45) Date of Patent: *Oct. 16, 2007

(54) PROCESS AND APPARATUS FOR THE ISOLATION OF PURE, OR SUBSTANTIALLY PURE, ORGANOMETALLIC COMPOUNDS

(75) Inventors: Rajesh Odedra, Cheshire (GB); Megan Ravetz, Chester (GB); Graham Williams, Wirral (GB); Phillip Reeve Jacobs, Cheshire (GB)

(73) Assignee: Sigma-Aldrich Co., St Louis, MO (US)

( * ) Notice: Subject to any disclaimer, the term of this patent is extended or adjusted under 35 U.S.C. 154(b) by 342 days.

This patent is subject to a terminal disclaimer.

(21) Appl. No.: 10/333,569

(22) PCT Filed: Mar. 5, 2001

(86) PCT No.: PCT/GB01/00906

§ 371 (c)(1),
(2), (4) Date: Jul. 23, 2003

(87) PCT Pub. No.: WO02/07848

PCT Pub. Date: Jan. 31, 2002

(65) Prior Publication Data

US 2004/0254389 A1    Dec. 16, 2004

(30) Foreign Application Priority Data

Jul. 22, 2000 (GB) ................. 0017968.9

(51) Int. Cl.
*B01D 3/00* (2006.01)
*C07F 5/00* (2006.01)

(52) U.S. Cl. ............ 203/29; 91/DIG. 19; 91/99; 556/1; 556/187

(58) Field of Classification Search ........... 203/1, 203/2, 29, 99, DIG. 19, 91; 556/1, 187
See application file for complete search history.

(56) References Cited

U.S. PATENT DOCUMENTS

| | | | |
|---|---|---|---|
| 3,230,245 A | | 1/1966 | Binning et al. |
| 3,734,941 A | * | 5/1973 | Sydor ............ 560/345 |
| 4,081,472 A | * | 3/1978 | Tsumura et al. ...... 560/345 |
| 4,487,713 A | * | 12/1984 | Spohn ............ 560/345 |
| 4,623,432 A | * | 11/1986 | Ali ................ 203/98 |
| 5,336,473 A | | 8/1994 | Nadler et al. |
| 6,495,707 B1 | * | 12/2002 | Leese et al. ........ 556/1 |

OTHER PUBLICATIONS

International Search Report for International Application No. PCT/GB 01/00906 dated May 31, 2001.

(Continued)

*Primary Examiner*—Virginia Manoharan
(74) *Attorney, Agent, or Firm*—Jeffrey A Wilson

(57) ABSTRACT

A process and apparatus to enable the continuous isolation of an organometallic compound, such as trimethylindium from a liquid feedstock. The liquid feedstock is delivered to a distillation column having two heating zones to effect dissociation of the feed stock thereby liberating the organometallic compound, which is collected as a vapor from the top of the column.

18 Claims, 1 Drawing Sheet

OTHER PUBLICATIONS

Figure 1:
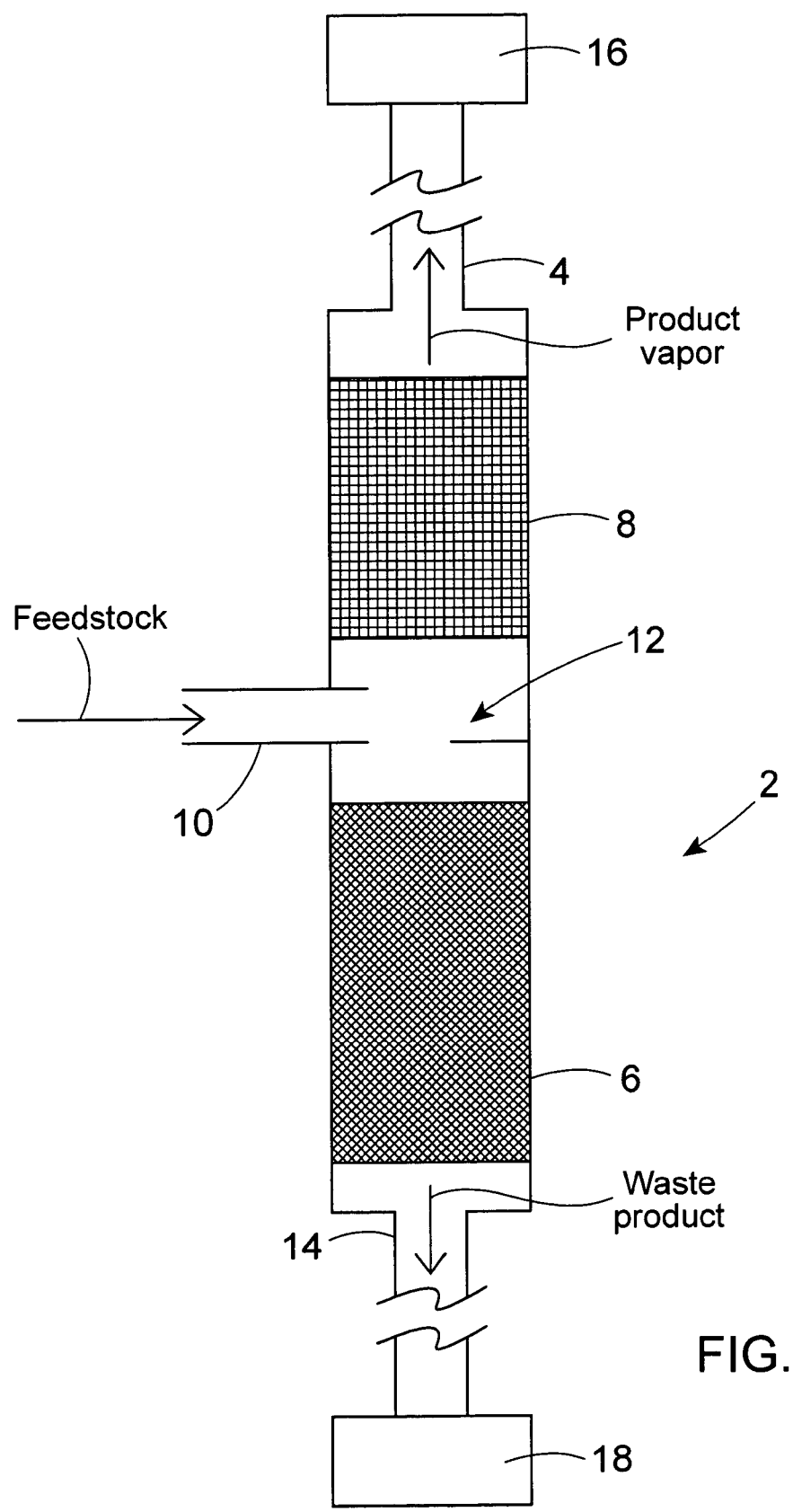

Perry, Malone H., Perry's Chemical Engineers' Handbook, 1984, McGraw-Hill Book Co.

Mohl K -D et al: "mehrfache Stationaere Betriebszustaende Bei Der Herstellung Des Kraftstoffethers Tame Durch Reaktivrektifikation—Teil 1: Theoretische Analyse" Chemie. Ingenieur. Technik, DE, Verlag Chemie GMBH. Weinheim, vol. 70, No. 5, May 1, 1998, pp. 524-527, XP000751679 ISSN: 009-286X Abbildung 1 p. 524*.

*The relevance of this reference is its citation in the International Search Report.

* cited by examiner

PROCESS AND APPARATUS FOR THE ISOLATION OF PURE, OR SUBSTANTIALLY PURE, ORGANOMETALLIC COMPOUNDS

The present invention relates to an improved process and apparatus for the isolation of pure, or substantially pure, organometallic compounds, in particular organo compounds of Group 3a metals, especially Trimethylindium.

Organometallic compounds, such as Trimethylindium, Trimethylgallium and Triethylgallium are commonly employed as metal sources in the fields of epitaxial semiconductor growth and/or processing, vapour or plasma etching, plasma deposition or thin film deposition, for example, Metalorganic Chemical Vapour Deposition (MOCVD). The compounds are generally isolated using a batch process wherein the reactants are fed into a vessel and the product is collected under the correct experimental conditions. Organometallic compounds are usually isolated from a liquid feedstock, which is formed in the production process, comprising the group 3a compound and a suitable ligand, for example, tetraglyme. Thermal dissociation of this feedstock liberates the desired product under mild conditions and leaves the less volatile components in the main vessel. This process provides compounds that are sufficiently pure but requires the use of large reaction vessels to produce sufficient yield of product. The production rate of the compound is also limited due to the necessity to charge the main vessel, collect the product and then clean out the vessel before commencing the process again. Cleaning equipment between runs may also lead to increased contamination of the product.

U.S. Pat. No. 5,336,473 (Nadler, K et al) describes an apparatus for removing cobalt values from a crude product using a stripper reactor wherein the crude product is fed to the top of the reactor. Such an arrangement would not be suitable for continuously isolating organometallic compounds such as trimethylindium.

It is an aim of the present invention to provide an improved process and apparatus for the isolation of pure, or substantially pure, organometallic compounds, in particular the isolation of Trimethylindium, which overcome the above mentioned drawbacks.

Accordingly, a first aspect of the present invention provides a continuous process for the isolation of an organometallic compound comprising. referring to FIG. 1, the steps of delivering a liquid feedstock containing the desired organometallic compound to a heated reaction centre 12 of a distillation column 2 allowing thermal dissociation of the feedstock to occur in a first heating zone 6 at or below the heated reaction centre 12 to liberate the organometallic compound in the vapour phase, passing the organometallic compound through a second heating zone 8 above the heated reaction centre 12 to maintain it in the vapour phase and collecting the isolated organometallic compound.

A second aspect of the present invention provides an apparatus for the continuous isolation of a substantially pure organometallic compound, referring to FIG. 1, the apparatus comprises a delivery conduit 10 for input of a liquid feedstock, a distillation column 2 and at least one outlet 4 the distillation column having at least one controllable heat source (not depicted) to provide a first heating zone 6 at or below the centre of the column, such as to cause thermal dissociation of the feedstock and vapourisation of the product and a second heating zone 8 above the centre of the column to prevent condensation of the vapourised product thereby enabling continuous collection of the vaporised product through the outlet 4.

The process of the present invention may be used to isolate any organometallic compound from a feedstock wherein the product is volatile and the by-products are less volatile.

Again referring to FIG. 1. the The process requires the feedstock to be fed into a distillation column 2, preferably into the centre of the column. An outlet 4 is preferably provided at or near the top of the column for the collection of the isolated product and a further outlet 14 is preferably provided at or near the base of the column for removal of waste products. A collection vessel 16 connected to the first outlet, is preferably provided for collection of the isolated product. Preferably, a second or further collection vessel 18 connected to the second outlet 14 is provided for collection of waste products.

The first selection vessel is preferably cooled prior to commencing the process. more preferably, the vessel is cooled to at least $-15°$ C., more preferably at least $-20°$ C.

The equipment is maintained at specified temperatures to control the rate of removal of the product from the top of the column. The continous delivery of the feedstock at a predetermined rate into the column, together with the maintenance of a specified temperature and pressure differential in the column enables a continuos production of the pure organometallic compound to be achieved. The rate of addition of the feedstock may be controlled by means of appropriate flow controllers, preferably liquid mass flow controllers.

The process is preferably carried out under vaccum, preferably at a pressure of at least 1 Torr ($133.32 Nm^{-2}$), more preferably at least 2 Torr ($266.64 Nm^{-2}$).

The continuos process relies on an equilibrium being set up in the column such that the product goes up the column and waste products move down. A number of factors effect the maintenance of this equilibrium, such as temperature of the column, the system pressure, the addition rate of the feedstock, and the removal rate of material from the column. The conditions employed will vary according to the feedstock composition and the organometallic compound being collected. Preferalby the temperature and/or pressure will remain fixed with the main control being the addition rate of the feedstock.

The distillation column for use in the process and apparatus of the present invention is equipped with two heating zones, a first heating one to dissociate the liquid feedstock and liberate the desired organometallic remains in the vapor phase and the other components are condensed. The temperatures of the respective heating zones will depend upon the feedstock being used and the organometallic compound to be isolated.

Any suitable distillation column may be used for carrying out the process of the present invention, such as packed or plate distillation columns. The column should be equipped with sufficient plates in the decomposition section to ensure maximum removal of product from feedstock and sufficient plates in the rectification section to ensure pure product leaves top of the column.

The reaction centre is preferably heated prior to commencing delivery of the feedstock in order to achieve efficient product seperation and steady state, Collection of product may be commenced immediately on addition of the feedstock but preferably is commenced after a constant temperature in the rectification column has been achieved. Preferably, collection of product is halted if a rise in temperature in the rectification column is observed indicating less volatile component boil up.

The process of the present invention is particularly suitable for the preparation of Trimethylindium in a continuous fashion. Preferably, the feedstock is the adducttrimethylindium tetraglyme. The ratio of trimethylindium to tetraglyme in said trimethylindium tetraglyme adduct is preferably in the range 2:1 to 3:1. The lower heating zone is preferably heated to 100°0 C.-140° C., more preferably 120° C. to 130° C. to achieve cracking of the adduct and to vapourise the trimethylindium. The upper heating zone is preferably heated to 30° C. to 60° C., more preferably at least ° C. to prevent condensation of trimethylindium as it passes up the column.

The present invention will now be further illustrated by means of the following Examples which describe the continuous preparation of Trimethylindium using the process and apparatus of the present invention and with reference to the accompanying drawing which is a schematic diagram of one embodiment of the present invention.

EXAMPLE 1

A main distillation column 2 was packed and placed under inert atmosphere using a series of vacuum/nitrogen cycles passed through the upper outlet 4 at the top of the column. A lower heated zone 6 was raised in temperature to 120° C. and a upper heated zone 8 raised to 60° C. The initial product collection vessel (not shown) was cooled to −20° C. A vacuum was then established in the system through the collection vessel of approximately 1 Torr (133.32 $Nm^{-2}$).

Once a steady state had been achieved, dosing of the feedstock through inlet 10 into the centre 12 of the column was begun at a rate of 7 ml/mm. The feedstock was an adduct of Trimethylindium (TMI) and Tetraglyme in a ratio of 2.25:1. Solid TMI was observed to be collected in the collection vessel, via the outlet 4, after several minutes once a liquid equilibrium had been established in the column.

After 3 hours, approximately 1.25 litres of feedstock had been added to the column with 500 g of solid TMI product collected from the top of the column. The waste product, a reduced ratio TMI Tetraglyme adduct, was removed from the bottom of the column into a separate vessel (not shown), via a lower outlet 14.

As the 1:1 TMI Tetraglyme adduct is thermally stable and thus will not liberate further TMI the process efficiency was calculated on the free TMI present in the feedstock and proved to be 84%.

EXAMPLE 2

The apparatus used in Example 1 above was employed without cleaning. Hence, the column was primed with feedstock/waste products from the start. The lower heated zone 6 was again raised in temperature to 120° C. but the upper heated zone 8 was raised to 40° C. All other procedures were the same except a vacuum of approximately 2.4 Torr (319.968 $Nm^{-2}$) was established in the system through the collection vessel and dosing of the TMI. Tetraglyme feedstock was begun at a rate of 4 ml/min in a ratio 2.3:1. Solid TMI was observed to be collected almost immediately as the liquid equilibrium in the column was established.

After 6.5 hours approximately 1.5 litres of feedstock had been added to the column with 450 g of solid TMI product collected from the top of the column. The waste product, a reduced ratio TMI. Tetraglyme adduct, was removed from the bottom of the column.

As the 1:1 TMI. Tetraglyme adduct is thermally stable and thus will not liberate further TMI the process efficiency was calculated on the free TMI present in the feedstock and proved to be 70%.

EXAMPLE 3

The process described in Example 1 above was repeated. The lower heated zone was again raised in temperature to 120° C. but the upper heated zone was raised to 40° C. A vacuum of approximately 2 Torr (266.64 $Nm^{-2}$) was established and once a steady state had been achieved, dosing of the TMI. Tetraglyme feedstock (in a ratio 2.3:1) was begun at a rate of 2 ml/min. Solid TMI was observed to be collected after several minutes once a liquid equilibrium had been established in the column.

After 8 hours approximately 1 litre of feedstock had been added to the column with 390 g of solid TMI product collected from the top of the column. The waste product, a reduced ratio TMI. Tetraglyme adduct, was removed from the bottom of the column.

As the 1:1 TMI. Tetraglyme adduct is thermally stable and thus will not liberate further TMI the process efficiency was calculated on the free TMI present in the feedstock and proved to be 96%.

The process and apparatus of the present invention enable the continuous isolation of an organometallic compound to be achieved with sufficient yields of product. This allows the ready scale up of the process without the need for huge plant vessels and additional processing steps. The continuous process allows the use of much smaller vessels, for example 10 L holding vessels as opposed to 200 L vessels, to produce a similar rate of production with associated safety benefits. Additionally the process avoids the need for frequent dismantling and cleaning of the equipment thereby reducing potential contamination of the product and again increasing production rates and improving safety ratings. The process and apparatus are applicable to both solid and liquid products using a suitable liquid feedstock.

The invention claimed is:

1. A continuous process for the isolation of an organometallic compound comprising the steps of delivering a liquid feedstock containing the desired organometallic compound to a heated reaction center of a distillation column, allowing thermal dissociation of the liquid feedstock to occur in a first heating zone at or below the heated reaction center to liberate the organometallic compound in the vapor phase, passing the liberated organometallic compound through a second heating zone above the heated reaction center to maintain it in the vapor phase and to isolate the organometallic compound, and collecting the isolated organometallic compound.

2. A continuous process as claimed in claim 1, wherein the isolated organometallic compound is volatile and waste products produced from the dissociation are less volatile.

3. A continuous process as claimed in claim 1, wherein the isolated organometallic compound is collected as a vapor at or near the top of the distillation column.

4. A continuous process as claimed in claim 1, wherein waste products are collected at or near the base of the distillation column.

5. A continuous process as clamed in claim 1, wherein the isolated organometallic compound is collected in a separate collection vessel that is cooled to at least −15°C.

6. A continuous process as claimed in claim 5, wherein the collection vessel is cooled to −20°C.

7. A continuous process as claimed in claim 1, further comprising maintaining specified temperatures in the distillation column to control the rate of removal of the isolated organometallic compound from the distillation column.

8. A continuous process as claimed in claim 1, further comprising establishing an equilibrium in the distillation column by maintaining specified temperatures and pressure differential in the distillation column and continuously delivering the feedstock to the distillation column at a controlled addition rate.

9. A continuous process as claimed in claim 8, wherein the temperatures, pressure differential, or both are kept fixed and the main control for the isolation of the organometallic compound is the addition rate of the feedstock.

10. A continuous process as claimed in claim 1, wherein the dissociation and isolation is carried out under vacuum.

11. A continuous process as claimed in claim 10, wherein the dissociation and isolation is carried out a pressure of at least 1 Torr (133.32 $Nm^{-2}$).

12. A continuous process as claimed in claim 1, wherein the first heating zone is kept at a higher temperature than the second heating zone.

13. A continuous process as claimed in claim 1, wherein the reaction center is heated prior to commencing delivery of the feedstock.

14. A continuous process as claimed in claim 1, wherein collection of the isolated organometallic compound is commenced after a constant temperature has been achieved in the distillation column.

15. A continuous process as claimed in claim 1, wherein the organometallic compound is trimethylindium.

16. A continuous process as claimed in claim 15 wherein the feedstock is a trimethylindium tetraglyme adduct.

17. A continuous process as claimed in claim 16 wherein the ratio of trimethylindium to tetraglyme in said trimethylindium tetraglyme adduct is in the range 2:1 to 3:1 .

18. A continuous process as claimed in claim 15 wherein the first heating zone is maintained at a temperature of between 100° C. and 140° C. and the second heating zone is maintained at a temperature of between 30° C. and 60°C.

* * * * *